US012667175B2

(12) United States Patent
Kamguia et al.

(10) Patent No.: US 12,667,175 B2
(45) Date of Patent: Jun. 30, 2026

(54) PROCESS FOR PERMANENT WAVING KERATIN FIBERS

(71) Applicant: KAO GERMANY GMBH, Darmstadt (DE)

(72) Inventors: Ruth Kamguia, Darmstadt (DE); Hans-Peter Laux, Darmstadt (DE); Jens Heilmann, Darmstadt (DE); Normen Lipinski, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 387 days.

(21) Appl. No.: 18/004,574

(22) PCT Filed: Jul. 7, 2021

(86) PCT No.: PCT/EP2021/068754
§ 371 (c)(1),
(2) Date: Jan. 6, 2023

(87) PCT Pub. No.: WO2022/008561
PCT Pub. Date: Jan. 13, 2022

(65) Prior Publication Data

US 2023/0240421 A1 Aug. 3, 2023

(30) Foreign Application Priority Data

Jul. 9, 2020 (EP) .................................... 20184963

(51) Int. Cl.

| | |
|---|---|
| ***A45D 7/06*** | (2006.01) |
| ***A61K 8/19*** | (2006.01) |
| ***A61K 8/36*** | (2006.01) |
| ***A61K 8/40*** | (2006.01) |
| ***A61Q 5/04*** | (2006.01) |

(52) U.S. Cl.
CPC .................. *A45D 7/06* (2013.01); *A61K 8/19* (2013.01); *A61K 8/36* (2013.01); *A61K 8/40* (2013.01); *A61Q 5/04* (2013.01)

(58) Field of Classification Search
None
See application file for complete search history.

(56) References Cited

U.S. PATENT DOCUMENTS

| | | | | | |
|---|---|---|---|---|---|
| 4,141,370 | A * | 2/1979 | Haas | A45D 2/148 132/245 |
| 2008/0142033 | A1 | 6/2008 | Sabbagh et al. | |
| 2020/0390215 | A1 | 12/2020 | Kibe et al. | |

FOREIGN PATENT DOCUMENTS

| | | | | |
|---|---|---|---|---|
| EP | 0 673 640 A1 | 9/1995 | |
| EP | 3476242 A1 * | 5/2019 | A45D 19/018 |
| EP | 3666340 A1 | 6/2020 | |
| JP | 03-153621 A | 7/1991 | |
| JP | 2007167192 A | 7/2007 | |
| JP | 2008061959 A * | 3/2008 | |
| JP | 2018153483 A | 10/2018 | |
| JP | 2019080721 A | 5/2019 | |
| WO | WO-2019096815 A1 * | 5/2019 | A61K 8/19 |
| WO | 2019/116805 A1 | 6/2019 | |
| WO | WO2019131734 A1 | 7/2019 | |
| WO | WO-2020120513 A1 * | 6/2020 | A45D 7/04 |

OTHER PUBLICATIONS

International Search Report dated Oct. 25, 2021, issued in connection with International Application No. PCT/EP2021/068754.
Written Opinion issued in connection with international Application No. PCT/EP2021/068754.
EP21742370.6—Communication Pursuant to Article 94(3) EPC, mailed on Mar. 3, 2026, 6 pages.

* cited by examiner

*Primary Examiner* — Celeste A Roney
(74) *Attorney, Agent, or Firm* — Norris McLaughlin, PA

(57) ABSTRACT

Processes and kits for permanent waving keratin fibers achieve durable shiny waves. The processes comprise treating fibers with a reducing composition, a non-reducing and non-oxidizing alkaline composition, optionally and acidic composition and finally an oxidizing composition, wherein, after processing the reducing composition, the fibers are rinsed off and the fibers are inserted into a curler having a tubular body with a first opening located at the first end and a second opening located at the second end and, wherein the curler is configured to allow keratin fiber streak to be inserted from the first opening toward the second opening and it is capable of being rolled up.

17 Claims, 3 Drawing Sheets

PROCESS FOR PERMANENT WAVING KERATIN FIBERS

This application is the U.S. National Stage of International Application No. PCT/EP2021/068754, filed Jul. 7, 2021, which claims foreign priority benefits under 35 U.S.C. § 119 of European Application No. 20184963.5, filed Jul. 9, 2020, the disclosures of which are incorporated herein by reference. Present invention relates to a process for permanent waving keratin fibers, especially human hair, for achieving durable shiny waves.

BACKGROUND OF THE INVENTION

The well-known and commonly used process for permanent waving keratin fibers involves reducing and oxidizing steps, which is often perceived as fiber damaging and the results are very much dependent upon how the whole process is carried out.

The fiber damage is especially due to the inappropriately selected, if not adjusted, processing period of the reducing composition. The hair may easily become over processed and appear, therefore, to have less strength, be brittle, not naturally feeling upon touching and especially less shiny so that hair looks dull.

Another aspect is that the use and/or the need of heat application during processing of the reducing agent on the fibers. This is usually realized with an external electrical heating devices and, especially in Asian geography, a specially therefore designed machine so called heat perming machine is used. It is the observation of the applicant that unless the pre-reduced hair is processed with heat, almost no curls are obtained although the hair is considerably damaged. There is highly need for simplified and non-damaging processes for obtaining strong, natural feeling, homogenous permanent waving.

The EP 673 640 discloses a process for permanent waving hair wherein hair is treated with a reducing composition for a period of 20 min and, without rinsing off, an alkaline composition was applied comprising alkali carbonates and hydrogen carbonates for a period of 10 min and finally hair is applied an aqueous oxidizing composition. It has been observed that the process described therein does not deliver cosmetically acceptable hair qualities in terms of waving efficiency and especially in smoothness, softness and shiny appearance.

Furthermore, JP-H03-153621 discloses a permanent shaping process wherein an acidic composition is mixed with an alkaline reducing agent composition and applied onto hair and after certain processing time an oxidizing composition is applied onto hair. The process does not deliver cosmetically appealing curls and hair qualities.

Similar process to the above is disclosed in US2008/0142033 wherein after treating hair with reducing composition, a composition comprising monovalent cation salt of organic acids is applied and finally hair is oxidized. This process as well have drawbacks in delivering less damage and effective curling to the hair which at the same time feels soft and smooth upon touching and appear shiny.

Another drawback of the currently available technologies is that any composition applied onto hair is penetrating into hair very fast which changes fiber environment drastically in terms of pH, reductive or oxidative environment. These sudden changes results in fast reactions within the fiber which leads to increased hair damage and therefore the hair does not feel healthy and does not appear shiny.

European patent applications of the present applicant with application numbers EP17202293 and EP18211548 are on permanent shaping keratin fibers with low damage on hair. Both documents disclose processes with conventional curlers and do not disclose curlers which may be rolled up or even self-rolling.

SUMMARY OF THE INVENTION

The inventors of the present invention have unexpectedly found out that using curlers capable of being rolled up in a permanent hair shaping process deliver more shiny hair which is perceived as healthier. The hair waved with such processes using curlers capable of being rolled up feels natural upon touching, has natural appearance with homogenous and intensive bouncy curls.

Thus, the first object of the present invention is a process for permanent waving keratin fibers, especially human hair, wherein, a—optionally, the fibers are washed and/or shampooed, and towel dried,
b—an aqueous composition comprising one or more reducing agent is applied and left on the fibers for a period of 1 to 60 min,
c—the fibers are rinsed off,
d—the fibers are inserted into curlers,
e—a non-reducing and non-oxidizing aqueous composition comprising one or more alkalizing agent and having an alkaline pH is applied onto fibers and left on the fibers for a period 1 to 60 min,
f—optionally the fibers are rinsed off,
g—an aqueous composition comprising one or more oxidizing agents, preferably hydrogen peroxide or bromate salt, is applied onto fibers and left on the fibers for a period 1 to 30 min,
h—the fibers are optionally rinsed off, and
i—the fibers are dried, wherein the curlers are taken off from fibers before or during processing in step g or after the step g prior to rinsing off and/or drying or after rinsing off (after step h), wherein the curlers of step d have a tubular body with a first opening located at the first end and a second opening located at the second end, and wherein the curlers are configured to allow a keratin fiber streak to be inserted from the first opening toward the second opening, and wherein the curlers are configured to be capable of being rolled up.

The second object of the present invention is the use of the process of the present invention for achieving natural, intensive, homogeneous and shiny waves on keratin fibers, especially human hair.

The third object of the present invention is a kit for keratin fibers, especially human hair, comprising three compositions and a curler wherein the first composition is an aqueous composition comprising one or more reducing agents as defined above, a non-reducing and non-oxidizing aqueous alkaline composition comprising one or more alkalizing agents as defined above and an aqueous composition comprising one or more oxidizing agents, preferably hydrogen peroxide or a bromate salt, as defined above, and one or more curler(s) as defined above, and optionally an acidic composition comprising one or more organic and/or inorganic acids.

BRIEF DESCRIPTION OF THE DRAWINGS

FIG. 1 FIGS. 1A and 1B are a front view and a rear view of the curler, respectively, showing one version of the curler that is used in a hair treatment method of the present invention.

FIGS. 3 FIGS. 3A and 3B are explanatory figures illustrating a procedure for performing the hair treatment method of the present invention using the curler shown in FIGS. 1A and 1B.

DETAILED DESCRIPTION OF THE INVENTION

Figure 1A:
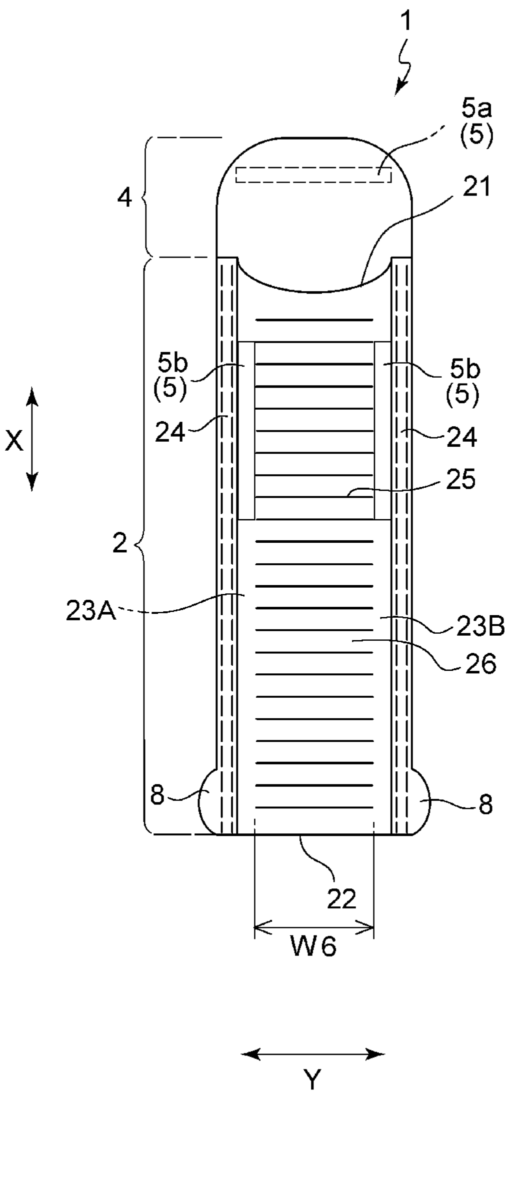

In a further preferred embodiment of the present invention, the whole process is carried out at ambient temperature without using any heat and/or heating device.

Without being bound by the theory, this should even further be beneficial to reduce hair damage and, therefore, contribute to healthy appearance and feeling of the fibers and leading to more shiny fibers.

In the process of the present invention, an aqueous composition comprising one or more reducing agents is applied onto fibers. In principal any reducing agent of inorganic and organic ones and their mixtures are suitable for the purpose of the present invention. The preferred ones are inorganic and organic reducing agents.

Suitable inorganic reducing agents are sulfite and/or hydrogen sulfite salts such as sodium, potassium, ammonium and suitable organic reducing agents are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and their mixtures. Preferred are thioglycolic acid and/or its salts, thiolactic acid and/or its salts, cysteine or its derivatives and/or its salts and sodium, potassium, ammonium sulfites and their mixtures. The most preferred are thioglycolic acid and/or its salts and sodium, potassium, ammonium sulfites, and their mixtures.

The total concentration of reducing agents in the aqueous composition of step b is in the range of 0.5 to 20%, preferably 1 to 15%, more preferably 2 to 12% and most preferably 3 to 10% by weight calculated to the total of the aqueous composition.

The pH of the composition may be acidic or alkaline and preferably in the range of 3 to 12, more preferably 4 to 11 and most preferably it is alkaline and in the range of 7.5 to 10.5. The pH may be adjusted with the known organic and/or inorganic acids and alkalizing agents (see below).

The aqueous composition comprising one or more reducing agents is left on the hair for a period of 1 to 60 min, preferably 2 to 45 min, more preferably 5 to 30 min and most preferably 5 to 20 min at ambient temperature and without using any heat and/or heating device.

After rinsing off the fibers, the fibers are inserted into curlers having tubular body being able to be rolled up as described above.

Figure 1B:
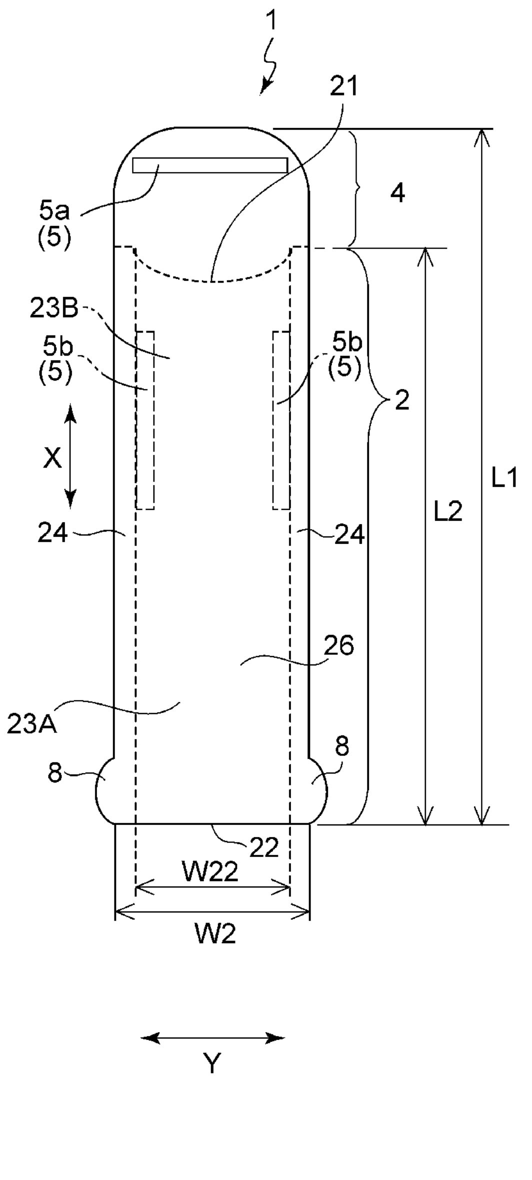

FIGS. 1A and 1B show an embodiment of the curler that is used in the hair treatment method of the present invention. The curler 1 comprises first and second tabs 8 and is configured to allow a lock of hair to be inserted from an opening 21 located at a first end toward an opening 22 located at a second end. Specifically, the tubular body 2 is formed by two sheets 23A and 23B that are elongated in one direction, the two sheets serving as a first surface sheet 23A and a second surface sheet 23B, which will be described later, and has a flat shape in which the two sheets 23A and 23B are laid one on top of the other. The tubular body 2 has a pair of side joint portions 24 where the first surface sheet 23A and the second surface sheet 23B are joined to each other, and a tubular portion 26 that is located between the pair of side joint portions 24. Each of the pair of side joint portions 24 are formed by joining side edge portions of the two sheets 23A and 23B to each other along the extending direction along which the sheets 23A and 23B extend. The tubular portion 26 has, between the opening 21 located at the first end and the opening 22 located at the second end in a longitudinal direction X, a space into which the lock of hair can be inserted. For the present aspect, the side joint portions 24 are formed with sewing using a sewing thread.

Figure 2:
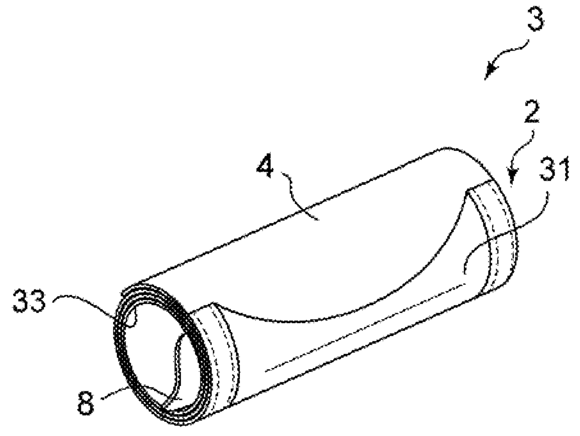
FIG. 2 FIG. 2 is a perspective view showing the curler shown in FIGS. 1A and 1B in a state in which the curler is rolled up.
Figure 3A:
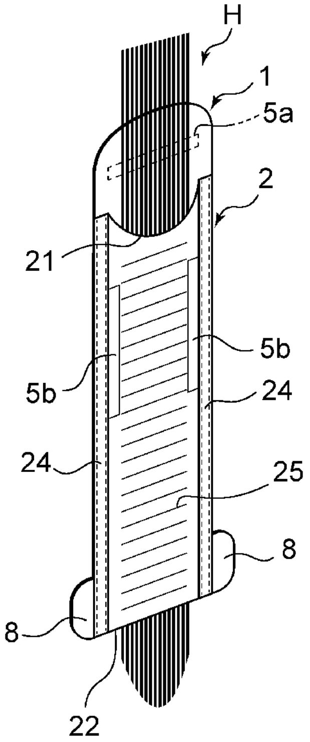
Figure 3B:
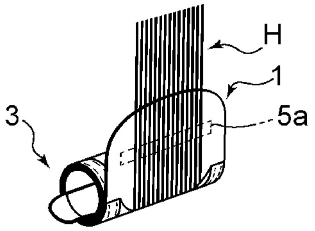

The tubular body 2 is configured to be capable of being rolled up. Being configured to be capable of being rolled up means that the tubular body 2 can be rolled into a roll shape as shown in FIG. 2. Such a configuration is preferably a configuration in which the tubular body 2 automatically rolls up, but may also be a configuration in which the tubular body 2 is manually rolled up. An example of the automatic rolling-up configuration is a configuration in which the tubular body 2 is wound in a roll shape in its natural state, and after stretching out the tubular body 2 and inserting a lock of hair therein, the tubular body 2 rolls up together with the lock of hair upon being released from the stretched state. Such a configuration can be realized in such a manner that either or both of the first surface sheet 23A and the second surface sheet 23B is made of a shape memory sheet that has preliminarily retained the state in which the curler 1 is rolled up. The shape memory sheet can be formed by bonding together films having different heat shrinkage rates or films having different tensions, for example. Moreover, the tubular body 2 may also return to its retained original roll shape when the sheets 23A and 23B constituting the tubular body 2 are heated. "In its natural state" as used herein means the state that the hair holder where no eternal force is applied is horizontally placed in the environment of temperature of 20° C. and humidity of 40%.

In the rolled-up state as displayed in FIG. 2, the body of the curler 3 has an outer circumferential portion 31 and a portion 33 that is located nearer to the center than the outer circumferential portion 31. The portion 33 that is located nearer to the center will also be referred to as the "center-side portion 33". The outer circumferential portion 31 is a wound portion that is the farthest from the central axis in the tubular body 2 in a wound state, that is, a state in which it is rolled up into a roll, and is a portion that has the greatest roll diameter in the tubular body 2. The center-side portion 33 is a wound portion that is relatively near to the central axis compared with the outer circumferential portion 31, and has a smaller roll diameter than the outer circumferential portion 31. The number of turns of the wound portion that constitutes the center-side portion 33 may be no more than one, or equal to one, or may be two or more. The center-side portion 33 of the curler body 3 shown in FIG. 2 is constituted by a wound portion formed of three turns. However, other turn number are possible as they may be desired by the consumer to create a different wave shape.

A sheet that is located on the inside when the tubular body 2 is rolled up is also referred to as the first surface sheet 23A, and a sheet that is located on the outside when the tubular body 2 is rolled up is also referred to as the second surface sheet 23B.

Examples of the material for forming a sheet constituting the tubular body include a nonwoven fabric (polyethylene nonwoven fabric, polyethylene terephthalate nonwoven fabric, or the like), a woven fabric, a net-like sheet, a porous or non-porous resin film (polyethylene film, polyethylene terephthalate film, or the like), paper, a polymer material sheet, a rubber sheet, a composite of these materials, or the like.

The thickness of each of the first surface sheet and the second surface sheet is preferably 5 μm or greater and more preferably 10 μm or greater, is preferably 2,000 μm or less and more preferably 1,500 μm or less, and is preferably from 5 to 2,000 μm and more preferably from 10 to 1,500 μm.

Preferably, a sheet that constitutes the tubular body (2) is subjected to processing for improving the diffusibility of the hair treatment agent such as a permanent wave agent. Examples of this processing include, but are not limited to, embossing, calendering, resin film formation, and the like. For example, the embossing can improve the diffusibility by forming protrusions successively arranged in the longitudinal direction of the sheet and thereby allowing the hair treatment agent to flow along the protrusions. The calendering can improve the diffusibility of the hair treatment agent by adjusting the density of the sheet that constitutes the tubular body. The resin film formation can improve the diffusibility of the hair treatment agent by forming a resin film with low liquid absorbency partially or entirely on the sheet that constitutes the tubular body and thereby reducing the total liquid absorption amount of the sheet.

It is further preferred from the viewpoint of improving the ease of the curling operation, that the curler has fixing means. For example, as shown in FIGS. 1A and 1B, the curler 1 has the fixing member 5 that maintains the tubular body 2 in a rolled-up form, and the fixing member 5 has a first member 5*a* and second member 5*b* that can be detachably joined together. The first member 5*a* and the second members 5*b* are provided at positions where, in the tubular body 2 in the rolled-up form, the first member Sa partially opposes the second members 5*b*. For example, the first member 5*a* is provided on an outer surface of the first surface sheet 23A, and the second members 5*b* are provided on an outer surface of the second surface sheet 23B. The "outer surfaces" means the surfaces on the opposite side to the surfaces that form the space into which the hair can be inserted. When the tubular body 2 is rolled-up, the outer surface of the first surface sheet 23A and the outer surface of the second surface sheet 23B partially oppose each other, and the first member 5*a* and the second members 5*b* that are located in the opposing portions can be joined together. In the present embodiment, the first member 5*a* is located in a portion on the outer surface of the first surface sheet 23A, the portion constituting the outer circumferential portion 31 of the tubular body 2 when the tubular body 2 is rolled-up, and the second members 5*b* are located on the outer surface of the second surface sheet 23B, the wound portion being adjacent to the outer circumferential portion 31.

Any fastener can be suitably used as the fixing member 5. The fastener is a joint member, or a male and female member. The joint member, and the male and female member are constituted by a plurality of members that can be detachably joined to each other. Examples of the joint member include an adherent-selective pressure-sensitive adhesive tape, a magnet, and the like. Examples of the male and female member include a hook and eye, a mechanical hook-and-loop fastener, and the like.

The adherent-selective pressure-sensitive adhesive tape is a pressure-sensitive adhesive tape that adheres only to a particular substance and substantially does not adhere to any other substances. The wording "substantially does not adhere" includes not only a case where the adherent-selective pressure-sensitive adhesive tape does not create an adhesion state with any substance other than the particular substance but also a case where, even though the adherent-selective pressure-sensitive adhesive tape creates an adhesion state with a substance other than the particular substance, the adhesion state quickly disappears if a slight relative movement occurs between that substance and the adherent-selective pressure-sensitive adhesive tape. Such an adherent-selective pressure-sensitive adhesive tape includes a tape base material and a self-adhesive agent applied to the tape base material, and the self-adhesive agent adheres only to a substance of the same kind and substantially does not adhere to other substances. In summary, the self-adhesive agent has adhesiveness only to the self-adhesive agent itself.

As an example of the adherent-selective pressure-sensitive adhesive tape having the above-described configuration, a pressure-sensitive adhesive tape including a self-adhesive agent and a tape base material disclosed in JP 2007-167192A can be used.

Suitable curlers are disclosed in patent application series of Kao Corporation such as EP3476242, WO2019116805, WO2019131734, JP2018153483, and JP2019080721.

After inserting the hair into the curler and rolling up the curler, the hair is applied a non-reducing and non-oxidizing aqueous composition comprising one or more alkalizing agents. The composition is left on the hair for a period of 1 to 60 min, preferably 2 to 45 min, more preferably 5 to 30 min and most preferably 5 to 20 min at ambient temperature and without using any heat and/or heating device.

The suitable alkalizing agents may be inorganic and organic ones and all well-known agents in the art are suitable for the purpose of the present process. The pH of the composition is in the range of 7.5 to 12, preferably 8 to 11, more preferably 8.5 to 10.5 and most preferably 8.5 to 10. The pH may be adjusted by selecting the concentration of the alkalizing agent for achieving the required pH or alternatively may be adjusted using inorganic and/or organic acids.

The concentration of the alkalizing agents is adjusted as their $NH_3$ equivalent which may easily be determined by titrating the alkaline solution with a standard acidic solution and calculating the molar concentration of the alkalizing agent which is then expressed as molar equivalent $NH_3$. Finally, from the molar equivalent and from the molecular weight of $NH_3$, the concentration in % is calculated. The titration is carried out at ambient temperature i.e. at approximately 20° C. Accordingly, the ammonia equivalent concentration must be in the range of 0.1 to 15%, preferably 0.1 to 12.5%, more preferably 0.25 to 10% and most preferably 0.5 to 8% by weight calculated to the total of the composition as ammonia equivalent determined by titration method at ambient temperature.

Suitable alkalizing agents are the alkali hydroxides such as sodium hydroxide, potassium hydroxide, ammonia and its salts such as ammonium carbonate, ammonium hydrogen carbonate, ammonium carbamate, ammonium chloride, ammonium sulfate, ammonium phosphates such as ammonium dihydrogen phosphate, diammonium hydrogen phosphate, diammonium sodium phosphate, ammonium sodium hydrogen phosphate or ammonium disodium phosphate, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate, guanidine and its salts such as guanidine hydrochloride, guanidine carbonate, guanidine bicarbonate, and an alkyl or alkanol amine according to the general structure

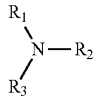

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, such as monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine and amino methyl propanol and their mixtures.

Preferred are ammonia and its salts, monoethanolamine, diethanolamine, triethanolamine, amino methyl propanol, guanidine salts and their mixtures. The most preferred are ammonia, ammonium chloride, guanidine carbonate, monoethanolamine and amino methyl propanol and their mixtures.

After optionally rinsing off the aqueous composition comprising alkalizing agents, an aqueous composition comprising one or more oxidizing agents, preferably hydrogen peroxide or a bromate salt is applied onto hair and left on the hair for 0.5 to 30 min, preferably 2 to 25 min, more preferably 3 to 20 min and most preferably 5 to 15 min at ambient temperature without application of any heat and/or heating device.

The fibers are preferably rinsed off at the end of the above-referred processing time. Optionally the oxidizing composition may also be left on the hair, i.e. not rinsed off from hair.

The total concentration of one or more oxidizing agents, preferably hydrogen peroxide or bromate salt, in the aqueous composition is in the range of 0.1 to 15%, preferably 0.2 to 12.5%, more preferably 0.25 to 10% and most preferably 0.5 to 8% by weight calculated to the total of the aqueous composition.

In general, the pH of the oxidizing composition is in the range of 2 to 8. The pH of the composition is depending on the oxidizing agent comprised in the composition. In case of hydrogen peroxide a pH in the range of 2 to 6 is suitable. In case of sodium bromate a pH of 5 to 8 is suitable. pH of the composition may be adjusted using inorganic and/or organic acids and bases well known in the art.

The curlers are being taken off from hair prior to application of the aqueous oxidizing composition or during the time the aqueous composition is left on the hair or after rinsing off the aqueous oxidizing composition. The preferred is the curlers are taken off from hair after rinsing off the aqueous oxidizing composition.

In case that the aqueous oxidizing composition is not rinsed off from hair, the curlers may be taken off from hair either after application of the oxidizing composition or prior to application of the oxidizing composition.

In a further preferred embodiment of the present invention, after step e or prior to step g, a non-reducing and non-oxidizing aqueous composition is applied onto fibers comprising one or more organic and/or inorganic acids and having a pH in the range of 2 to 6.5 and optionally left on the hair for a period 1 to 60 min, which is optionally the fibers are rinsed off. pH of the composition is preferably in the range of 2.5 to 5.5, more preferably 2.5 to 5 and most preferably 3 to 4.5.

The acidic composition comprising one or more organic and/or inorganic acids is optionally left on the hair for a period of 1 to 60 min, preferably 2 to 45 min, more preferably 5 to 30 min and most preferably 5 to 20 min at ambient temperature and without using any heat and/or heating device.

Suitable organic acids are citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts. Preferred are citric acid, lactic acid, succinic acid, malic acid and their salts.

Suitable inorganic acids are phosphoric acid, hydrochloric acid, sulfuric acid, carbonic acid and their respective salts. Preferred are phosphoric acid and its respective salts.

The total concentration of acids is in the range of 0.1 to 20%, preferably 0.25 to 17.5% more preferably 1 to 15% and most preferably 2.5 to 15% by weight, calculated to the total of the composition.

In a further preferred embodiment of the present invention, in order to obtain optimal permanent shaping results, the alkalinity and acidity of the aqueous non-oxidizing/non-reducing alkaline and acidic compositions are so adjusted that the 1:1, by weight, (equal amount) mixture of the two compositions has a pH in the range of 4.5 to 8, preferably 5 to 7 and more preferably 5 to 6.5.

In the following, all reported concentrations must be understood as relative to each of the compositions because, firstly, the compositions are not mixed with each other and secondly, the same ingredient disclosed must not be comprised in all of the composition, although this is a possibility.

Aqueous compositions, all four or three or one or two advantageously comprise a thickening agent, preferably a thickening polymer. Suitable and preferred ones are thickening polymers such as polysaccharides such as alginate, pectinate, xanthan, hydroxypropyl xanthan or dehydroxanthan, non-ionic polysaccharides such as cellulose ethers (e.g., methylcellulose, hydroxyethylcellulose (HEC), methyl hydroxyethylcellulose (MHEC), ethyl hydroxyethylcellulose (EHEC), methyl ethyl hydroxyethylcellulose (MEHEC)), starch or dextrins. Synthetic acrylate type of thickeners may as well be comprised such as acrylate copolymers and alkyl acrylates homo or copolymers also known as associative thickeners.

The concentration of the thickening polymer is very much dependent on the type of the thickening polymer and the targeted consistency (viscosity) of the compositions. Typically, the thickening polymers are comprised in the compositions at a concentration in the range of 0.1 to 3%, preferably 0.25 to 2% by weight calculated to the total of each of the composition.

Aqueous compositions, all four, or three or one or two can comprise one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol, octyl dodecanol, cetostearyl alcohol, and their mixtures.

The total concentration of fatty alcohol is in the range from 0.5 to 15%, preferably 1 to 10% by weight, calculated to total of each of the composition.

Aqueous compositions, all four or three or one or two, advantageously comprise one or more surfactants. Suitable ones are selected from anionic, non-ionic, amphoteric and cationic ones.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfonation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

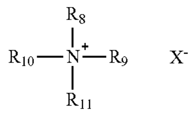

wherein $R_8$ is a saturated or unsaturated, branched or linear alkyl chain with 8-22 C atoms or $R_{12}CONH(CH_2)_n$ where $R_{12}$ is saturated or unsaturated, branched or linear alkyl chain with 7-21 C atoms and n has typical value of 1-4 or $R_{13}COO(CH_2)_n$ where $R_{13}$ is saturated or unsaturated, branched or linear alkyl chain with 7-21 C atoms and n has typical value of 1-4, and $R_9$ is H or unsaturated or saturated, branched or linear alkyl chain with 1-22 C atoms or $R_{12}CONH(CH_2)_n$ or $R_{13}COO(CH_2)_n$ where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonium chloride, dioleoylethyl dimethyl ammonium methosulfate, dioleoylethyl hydroxyethylmonium methosulfate.

The total concentration of one or more surfactants is in the range of 0.1 to 12.5%, preferably 0.2 to 10% and more preferably 0.5-7.5% by weight, calculated to the total of each of the composition.

Further advantageously, aqueous compositions, all four or three or one or two, comprise one or more silicone compound, preferably silicone oil. Suitable and preferred ones are known with their CTFA adopted name as dimethicone and commercially available from Dow Corning under the trade name DC 200 with various viscosities.

Further advantageously, aqueous compositions, all four or three or one or two, comprise one or more cationic polymers as conditioning and/or thickening agents.

Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride.

Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Preferred are Polyquaternium-2, Polyquaternium-6 and Polyquaternium 16.

The total concentration of cationic polymers may be in the range of 0.1-2.5%, preferably 0.25-2% by weight and more preferably 0.5-1.5% by weight, calculated to total of each of the composition.

Further advantageously, aqueous compositions all four or three or one or two comprise one or more aminated silicones which may be selected from amodimethicones and grafted aminated silicones. Suitable ones are available under various trade names such as DC 969, Belsil from Wacker Chemie AG and know with the CTFA adopted name Amodimethicone, and Elastomer OS from Kao Corporation known with CTFA adopted name Polysilicone-9.

Furthermore, aqueous compositions, all four or three or one or two, comprise one or more organic solvent which may act as penetration enhancer and/or solubilizing agent for the compounds not readily soluble in the aqueous medium. The suitable ones are 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol.

Concentration of one or more organic solvent is in the range of 0.1 to 15%, preferably 0.5 to 12.5% and more preferably 1 to 10% and most preferably 1 to 7.5% by weight calculated to the total of each of the composition.

The aqueous compositions, all four or three or one or two may advantageously comprise urea, at a concentration in the range of 0.1 to 20%, preferably 1 to 15% by weight, calculated to the total of the compositions.

Additionally, the aqueous compositions, all four or three or one or two, comprise one or more polyols. Suitable ones are glycerine, phytantriol, panthenol, ethyleneglycol, polyethyleneglycols, propylene glycols such as 1,2 propylene glycol, 1,3-propylene glycol and polypropylene glycols.

The total concentration of one or more polyol is in the range of 0.1 to 15%, preferably 0.25 to 12.5%, more preferably 0.5 to 10% and most preferably 1 to 7.5% by weight calculated to the total of each of the composition.

The aqueous compositions, all four or three or one or two, can comprise one or more amino acids and/or their water soluble salts. Suitable ones are glycine, histidine, citrullin, asaparagine, alanine, valine. Leucine, isoleucine, proline, tryptophan, phenylalanine, methinone, serine, tyrosine, threonine and glutamine.

The total concentration of one or more aminoacids and/or their water soluble salts is in the range of 0.01 to 2.5%, preferably 0.1 to 2%, more preferably 0.15 to 1.5% and most preferably 0.2 to 1% by weight calculated to the total of each of the composition.

Any of the compositions described in detail above may comprise ingredients customarily found in such compositions such as preservative, fragrance, chelating agents, radical scavenger, etc.

Following example to illustrate the invention, but not to limit it.

Example 1

| Aqueous reducing composition | % by weight |
|---|---|
| Ammonium thioglycolate | 10 |
| Ammonium hydroxide | 2 |
| Water | to 100 |

The pH of the above composition was adjusted to pH 9.0.

| Aqueous alkaline composition | % by weight |
|---|---|
| Ammonium hydroxide | 5 |
| Water | to 100 |

The pH of the above composition was adjusted to pH 9.9.

| Aqueous oxidizing composition | |
|---|---|
| Hydrogen peroxide | 3 |
| Phosphoric acid | q.s. to pH 3 |
| Water | to 100 |

Four hair streaks weighing approximately 5 g and having a length of 20 cm were permanently waved using the above compositions. Firstly, the streaks were washed with a commercially available shampoo compositions and towel dried. Afterwards, each streak was treated for 20 min with 4.5 g of the aqueous reducing composition, taken out and rinsed off with water. Afterwards, two streaks were put on conventional curlers with a diameter of 1.5 cm and the other two were inserted one by one into separate curlers with tubular body, which can be rolled up. Each streak on curlers was treated for 15 min with 4.5 g of the alkaline composition of above. After the processing time, the streaks were subsequently treated with the oxidizing composition for 10 min, the curlers were rinsed off for 5 min, taken off, and hair was dried.

Shine and alignment evaluations were carried out with an expert panel comprising six experts, which did not receive prior information on the treatment groups. They were asked to independently rate shine and alignment and to grade the hair streaks within a number range of 1 to 5, whereas 5 indicated the best performance and 1 the lowest performance. It was observed that all streaks on the Tubular body curler were shinier and better aligned.

| | Tubular body curler | | | | Conventional curler | | | |
|---|---|---|---|---|---|---|---|---|
| | alignment | | shine | | alignment | | shine | |
| Expert | Streak 1 | Streak 2 | Streak 1 | Streak 2 | Streak 1 | Streak 2 | Streak 1 | Streak 2 |
| No. 1 | 4 | 5 | 4 | 5 | 3 | 4 | 4 | 3 |
| No. 2 | 5 | 5 | 5 | 4 | 4 | 3 | 3 | 4 |
| No. 3 | 4 | 4 | 4 | 4 | 3 | 4 | 3 | 3 |
| No. 4 | 5 | 4 | 4 | 5 | 3 | 3 | 3 | 3 |
| No. 5 | 4 | 5 | 4 | 4 | 4 | 4 | 4 | 3 |
| No. 6 | 4 | 4 | 5 | 4 | 3 | 3 | 3 | 4 |
| average | 4.42 | | 4.33 | | 3.42 | | 3.33 | |
| STAW | 0.49 | | 0.47 | | 0.49 | | 0.47 | |

Example 2

| Aqueous reducing composition | |
|---|---|
| | % by weight |
| Ammonium thioglycolate | 10 |
| Ammonium hydroxide | 2 |
| Water | to 100 |

The pH of the above composition was adjusted to pH 8.5.

| Aqueous alkaline composition | |
|---|---|
| | % by weight |
| Ammonium chloride | 2 |
| Ammonium hydroxide | 4 |
| Water | to 100 |

The pH of the above composition was adjusted with sodium hydroxide to pH 10.0.

| Aqueous acidic composition | |
|---|---|
| | % by weight |
| Lactic acid | 8 |
| Water | to 100 |

The pH of the above composition was adjusted with sodium hydroxide to pH 3.5.

The 1 to 1, by weight, mixture of the aqueous alkaline and aqueous acidic compositions had a pH of approximately 6.0.

| Aqueous oxidizing composition | |
|---|---|
| Hydrogen peroxide | 3 |
| Phosphoric acid | q.s. to pH 3 |
| Water | to 100 |

Fourteen hair streaks weighing approximately 5 g each and having a length of 20 cm were permanently waved using the above compositions. Firstly, the streaks were washed with a commercially available shampoo compositions and towel dried. Afterwards, each streak was treated for 20 min with 4.5 g of the aqueous reducing composition, taken out and rinsed off with water. Afterwards, seven streaks were put on conventional curlers with a diameter of 1.5 cm and the other seven were inserted one by one into separate curlers with tubular body, which can be rolled up. All streaks on curlers were treated for 15 min with 4.5 g of the alkaline composition of above. Subsequently 4.5 g of the acidic composition was used for 3 min without rinsing on each streak. After the processing time all streaks were treated with the oxidizing composition for 10 min, the streak on curlers were rinsed off for 5 min, taken off, and the hair was dried. It was observed that all streaks were well waved.

Shine measurements were carried out with a system comprising a polarization camera, a polarized illumination and a cylindrical mount for the tresses. Illuminated light was measured under ambient conditions with all tresses separately.

The following results were obtained according to Bossa Nova method. This method retrieves the normalized shine intensity on a hair streak. Higher values represent higher shine intensity.

| Streak no | Conventional Curler | Tubular body Curler |
|---|---|---|
| 1 | 5.2 | 6.4 |
| 2 | 6.6 | 10.8 |
| 3 | 5.1 | 9.2 |
| 4 | 7.6 | 7.6 |
| 5 | 5.8 | 8.8 |
| 6 | 7.4 | 11.5 |
| 7 | 10.3 | 11.9 |
| Avarage | 6.9 | 9.5 |
| Standard deviation | 1.7 | 1.9 |
| p value at $p < 0.05$ | 0.0064 | |

Similar results were observed with the following examples.

Example 3

| | % by weight |
|---|---|
| Aqueous reducing composition | |
| Ammonium thioglycolate | 7 |
| Ammonium bicarbonate | 4 |
| Phosphoric acid | q.s. to pH 6.5 |
| Water | to 100 |
| Aqueous alkaline composition | |
| Ammonium bicarbonate | 4 |
| Sodium hydroxide | q.s. to pH 8.5 |
| Water | to 100 |

| Aqueous oxidizing composition | |
|---|---|
| | % by weight |
| Sodium bromate | 5 |
| Water | to 100 |

The above composition had a pH of 7.0.

Example 4

| Aqueous reducing composition | |
|---|---|
| | % by weight |
| Ammonium thioglycolate | 7 |
| Ammonium bicarbonate | 4 |
| Phosphoric acid | q.s. to pH 6.5 |
| Water | to 100 |

| Aqueous alkaline composition | |
|---|---|
| | % by weight |
| Ammonium bicarbonate | 4 |
| Sodium hydroxide | q.s. to pH 8.5 |
| Water | to 100 |

| Aqueous oxidizing composition | |
|---|---|
| | % by weight |
| Sodium bromate | 5 |
| Water | to 100 |

The above composition had a pH of 7.0.

Example 5

| Aqueous reducing composition | |
|---|---|
| | % by weight |
| Cetearyl alcohol | 10 |
| Oleyl alcohol | 5 |
| Thioglycolic acid | 1.7 |
| Ceteareth-20 | 1.0 |
| Hydroxyethylcellulose | 0.5 |
| EDTA | 0.5 |
| Fragrance | 0.5 |
| Aminomethylpropanol | q.s. to pH 9.0 |
| Water | to 100 |

| Aqueous alkaline aerosol foam composition | |
|---|---|
| | % by weight |
| Ammonium hydroxide | 5 |
| Ammonium chloride | 2 |
| Monoethanolamine | q.s. 9.0 |
| Cetrimonium chloride | 2 |
| Hydroxyethylcellulose | 0.5 |
| Water | to 100 |

The composition was filled in an aerosol can with 90% the above composition and 10% propane butane mixture as the propellant. The can was equipped with a foam dispensing actuator and head.

| Aqueous oxidizing composition | |
|---|---|
| | % by weight |
| Cetearyl alcohol | 5 |
| Behenrimonium chloride | 2 |
| Hydrogen peroxide | 3 |
| Phosphoric acid | to pH 3.0 |
| Water | to 100 |

Example 6

| Aqueous reducing composition | |
|---|---|
| | % by weight |
| Ammonium thioglycolate | 7 |
| Ammonium bicarbonate | 4 |
| Phosphoric acid | q.s. to pH 8.5 |
| Water | to 100 |

| Aqueous alkaline composition | |
|---|---|
| | % by weight |
| Ammonium bicarbonate | 4 |
| Sodium hydroxide | q.s. to pH 9.5 |
| Water | to 100 |

The pH of the above composition was adjusted to pH 9.5.

| Aqueous acidic composition | |
|---|---|
| Citric acid | 3 |
| Lactic acid | 3 |
| Succinic acid | 4 |
| Water | to 100 |

The pH of the above composition was adjusted to pH 3.5.

The 1 to 1, by weight, mixture of the aqueous alkaline and aqueous acidic compositions had a pH of approximately 5.5.

| Aqueous oxidizing composition | |
|---|---|
| | % by weight |
| Sodium bromate | 5 |
| Water | to 100 |

The pH of the above composition was adjusted with hydrochloric acid to pH 7.0.

Example 7

| Aqueous reducing composition | |
|---|---|
| | % by weight |
| Cetearyl alcohol | 10 |
| Oleyl alcohol | 5 |
| Thioglycolic acid | 3.7 |
| Ceteareth-20 | 1.0 |
| Hydroxyethylcellulose | 0.5 |
| EDTA | 0.5 |
| Fragrance | 0.5 |
| Aminomethylpropanol | q.s. to pH 8.5 |
| Water | to 100 |

| Aqueous alkaline aerosol foam composition | |
|---|---|
| | % by weight |
| Ammonium hydroxide | 5 |
| Ammonium chloride | 2 |
| Monoethanolamine | q.s. 9.8 |
| Cetrimonium chloride | 2 |
| Hydroxyethylcellulose | 0.5 |
| Water | to 100 |

The composition was filled in an aerosol can with 90% the above composition and 10% propane butane mixture as the propellant. The can was equipped with a foam dispensing actuator and head.

| Aqueous acidic composition | |
|---|---|
| Citric acid | 3 |
| Lactic acid | 4 |
| Succinic acid | 4 |
| Sodium cocamphoacetate | 0.1 |
| Polyquaternium-6 | 0.1 |
| Propylene glycol | 2.1 |
| Water | to 100 |

The pH of the above composition was adjusted with sodium hydroxide to pH 3.5.

| Aqueous oxidizing composition | % by weight |
|---|---|
| Cetearyl alcohol | 5 |
| Behenrimonium chloride | 2 |
| Hydrogen peroxide | 3 |
| Phosphoric acid | to pH 3.0 |
| Water | to 100 |

The invention claimed is:

1. A process for permanently waving keratin fibers comprising:

a—washing and towel drying fibers;

b—applying a first aqueous composition comprising one or more reducing agents onto the fibers and leaving the first aqueous composition on the fibers for a period of 1 to 60 minutes;

c—rinsing the first aqueous composition off the fibers;

d—inserting the fibers into a first opening of a curler toward a second opening of the curler and rolling or winding the curler onto itself to form a roll shape, wherein the curler comprising a tubular body has a total length defined between a first end and a second end opposite with respect to the first end, wherein the first opening is disposed at the first end of the tubular body and the second opening is disposed at the second end of the tubular body, wherein the tubular body has a total width defined between a first side edge and a second side edge opposite to the first side edge, the curler further comprises a first tab and a second tab, the first tab is disposed on the first side edge at the second end of the tubular body, and the second tab is disposed on the second side edge at the second end of the tubular body;

e—applying a non-reducing and non-oxidizing aqueous composition onto the fibers and leaving the non-reducing and non-oxidizing aqueous composition on the fibers for a period of 1 to 60 minutes, wherein the non-reducing and non-oxidizing aqueous composition comprises one or more alkalizing agents and has an alkaline pH;

f—optionally rinsing the non-reducing and non-oxidizing aqueous composition off the fibers;

g—applying a second aqueous composition comprising one or more oxidizing agents onto the fibers and leaving second aqueous composition on the fibers for a period of 1 to 30 minutes;

h—rinsing off the fibers; and i—drying the fibers, wherein the curlers are taken off from the fibers after step h—and before step i.

2. The process of claim 1, wherein the tubular body of the curler is formed by two sheets that are elongated in one direction, and the tubular body has a flat shape in which the two sheets are laid one on top of the other.

3. The process of claim 1, wherein at least one sheet of the two sheets is made of one or more materials selected from the group consisting of nonwoven fabric, woven fabric, a net-like sheet, a porous or non-porous resin film, paper, a polymer material sheet, a rubber sheet, a composite of said materials, and the at least one sheet has a thickness in the range of 5 μm to 2,000 μm.

4. The process of claim 1, wherein the one or more reducing agents are selected from sulfite and/or hydrogen sulfite salts, thiogylcolic acid and/or its salts, cysteamine and/or its salts, thioglycerin and/or its salts, glycerin esters of thioglycolic acid and/or its salts, thiolactic acid and/or its salts, cysteine and/or its salts, and at least one mixture thereof.

5. The process of claim 1, wherein the total concentration of the one or more reducing agents in the first aqueous composition is in the range of 0.5 to 20%, by weight, calculated to a total weight of the first aqueous composition.

6. The process of claim 1, wherein the first aqueous composition has a pH in the range of 3 to 12.

7. The process of claim 1, wherein the process, in its entirety, is carried out at ambient temperature without using any heat and/or heating device.

8. The process of claim 1, wherein the pH of the non-reducing and non-oxidizing aqueous alkaline composition is in the range of 7.5 to 12.

9. The process of claim 1, wherein the non-reducing and non-oxidizing aqueous alkaline composition comprises an alkalizing agent at an ammonia equivalent concentration of 0.1 to 15% by weight calculated to a total weight of the non-reducing and non-oxidizing aqueous alkaline composition as ammonia equivalent determined by titration method.

10. The process of claim 1, wherein the non-reducing and non-oxidizing aqueous alkaline composition comprises one or more alkalizing agents selected from sodium hydroxide, potassium hydroxide, ammonium carbonate, ammonium hydrogen carbonate, ammonium carbamate, ammonium chloride, ammonium sulfate, ammonium dihydrogen phosphate, diammonium hydrogen phosphate, diammonium sodium phosphate, ammonium sodium hydrogen phosphate or ammonium disodium phosphate, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate, guanidine hydrochloride, guanidine carbonate, guanidine bicarbonate, and an alkyl or alkanol amine according to the general structure

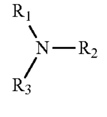

wherein $R_1$, $R_2$, and $R_5$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R^1$, $R^2$, or $R_3$ is different from H and selected from the group consisting of monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, diethanolpropylamine, monoethanolbutylamine, diethanolbutylamine, amino methyl propanol, and a mixture thereof.

11. The process of claim 1, wherein the pH of the second aqueous composition is in the range of 2 to 8, when hydrogen peroxide is comprised as oxidizing agent, and in the range of 5 to 8, when bromate salt is comprised in the composition.

12. The process of claim 1, wherein, after step e— or prior to step g—, an additional non-reducing and non-oxidizing aqueous composition is applied onto the fibers, comprising one or more organic and/or one or more inorganic acids, and has a pH in the range of 2 to 6.5 and is optionally left on the hair for a period 1 to 60 minutes, which is optionally rinsed off the fibers.

13. The process of claim 12 wherein the one or more organic acids are selected from citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts, and the one or more inorganic acids are selected from phosphoric acid, hydrochloric acid, sulfuric acid, carbonic acid and their respective salts.

14. The process of claim 12, wherein the one or more organic and/or the one or more inorganic acids are comprised at total concentration of in the range of 0.1 to 20% by weight, calculated to a total weight of the additional non-reducing and non-oxidizing aqueous alkaline composition with the condition the pH of a 1:1, by weight, mixture of the compositions used in steps e and the additional non-reducing and non-oxidizing aqueous alkaline composition comprising the one or more organic and/or the one or more inorganic acids is in the range of 4.5 to 8.

15. A kit for keratin fibers comprising three compositions and at least one curler, wherein a first composition of the three compositions is a first aqueous composition comprising one or more reducing agents, a second composition of the three composition is a non-reducing and non-oxidizing aqueous alkaline composition comprising one or more alkalizing agents, a third composition of three compositions is a second aqueous composition comprising one or more oxidizing agents, and the at least one curler is one of the curlers according to claim 1.

16. The process of claim 1, wherein the first tab and the second tab contact and/or terminate at the second end of the tubular body.

17. The process of claim 1, wherein the first tab and the second tab overlap each other in their entireties in a longitudinal direction along the total length of the curler.

* * * * *